(12) United States Patent
Park et al.

(10) Patent No.: US 11,318,063 B2
(45) Date of Patent: May 3, 2022

(54) APPARATUS FOR ASSISTING IN FINGER MOTION

(71) Applicant: NEOFECT CO., LTD., Yongin-si (KR)

(72) Inventors: Byeong Geol Park, Icheon-si (KR); Kyung Hwan Yoo, Incheon (KR); Young Geun Choi, Yongin-si (KR)

(73) Assignee: NEOFECT CO., LTD., Yongin-si (KR)

( * ) Notice: Subject to any disclaimer, the term of this patent is extended or adjusted under 35 U.S.C. 154(b) by 503 days.

(21) Appl. No.: 16/189,715

(22) Filed: Nov. 13, 2018

(65) Prior Publication Data
US 2019/0091091 A1    Mar. 28, 2019

Related U.S. Application Data

(63) Continuation of application No. PCT/KR2018/011270, filed on Sep. 21, 2018.

(30) Foreign Application Priority Data

Sep. 25, 2017   (KR) .................. 10-2017-0123417
Sep. 21, 2018   (KR) .................. 10-2018-0113751

(51) Int. Cl.
*A61H 1/02* (2006.01)
*A61F 5/01* (2006.01)

(52) U.S. Cl.
CPC .......... *A61H 1/0288* (2013.01); *A61F 5/013* (2013.01); *A61H 1/0218* (2013.01);
(Continued)

(58) Field of Classification Search
CPC .................. A61F 5/013; A61H 1/0288; A61H 2201/0153; A61H 2201/1215;
(Continued)

(56) References Cited

U.S. PATENT DOCUMENTS 5,697,103 A * 12/1997 Wiggins ........... A41D 19/01582
2/159
9,375,382 B2 * 6/2016 Fausti .................... A63B 23/16
(Continued)

FOREIGN PATENT DOCUMENTS

CN       105496728 A    4/2016
EP       2 417 941 A1   2/2012
(Continued)

OTHER PUBLICATIONS

An Office Action; "Notice of Reasons for Refusal", mailed by the Japanese Patent Office dated May 18, 2021, which corresponds to Japanese Patent Application No. 2020-516848 and is related to U.S. Appl. No. 16/189,715.
(Continued)

*Primary Examiner* — Tu A Vo
*Assistant Examiner* — Alexander Morales
(74) *Attorney, Agent, or Firm* — Studebaker & Brackett PC

(57) ABSTRACT

A finger-motion assisting apparatus. The apparatus includes a wearing part, a first cover extending from the wearing part to one side, first and second wires pulling the first cover, a pulley around which the first and second wires are wound, and a motor rotating the pulley. The first and second wires are arranged from a first point to a second point of the first cover along the extension direction of the first cover and arranged along at least part of a periphery of the first cover in opposite directions at the second point of the first cover.

10 Claims, 12 Drawing Sheets

(52) U.S. Cl.
CPC .............. *A61H 2201/0153* (2013.01); *A61H 2201/1215* (2013.01); *A61H 2201/149* (2013.01); *A61H 2201/165* (2013.01); *A61H 2201/1635* (2013.01); *A61H 2201/1638* (2013.01); *A61H 2201/1645* (2013.01); *A61H 2201/1652* (2013.01); *A61H 2201/1664* (2013.01); *A61H 2201/1671* (2013.01); *A61H 2201/1676* (2013.01); *A61H 2201/50* (2013.01); *A61H 2201/5097* (2013.01); *A61H 2205/065* (2013.01); *A61H 2205/067* (2013.01)

(58) Field of Classification Search
CPC ...... A61H 2201/149; A61H 2201/1635; A61H 2201/1638; A61H 2201/1645; A61H 2201/165; A61H 2201/1652; A61H 2201/1664; A61H 2201/1671; A61H 2201/1676; A61H 2201/5097; A61H 2205/065; A61H 2205/067; A61H 1/0285; A41D 19/0096; A41D 19/01582; A41D 19/01588
USPC ............................................ 601/40; 401/7, 8
See application file for complete search history.

(56) References Cited

U.S. PATENT DOCUMENTS

| | | | | |
|---|---|---|---|---|
| 10,248,200 | B2* | 4/2019 | Cohen | G06F 3/014 |
| 10,888,487 | B1* | 1/2021 | Rogers | A41D 19/0044 |
| 2006/0094989 | A1* | 5/2006 | Scott | A61F 2/586 |
| | | | | 601/5 |
| 2006/0224249 | A1 | 10/2006 | Winfrey | |
| 2010/0249675 | A1* | 9/2010 | Fujimoto | A61H 1/0285 |
| | | | | 601/40 |
| 2012/0022666 | A1* | 1/2012 | Brooks | A41D 19/01582 |
| | | | | 2/159 |
| 2012/0029399 | A1* | 2/2012 | Sankai | A61B 5/6812 |
| | | | | 601/40 |
| 2012/0167272 | A1* | 7/2012 | Scaff | A63B 21/4021 |
| | | | | 2/160 |
| 2013/0072829 | A1* | 3/2013 | Fausti | A63B 21/00178 |
| | | | | 601/40 |
| 2015/0190246 | A1* | 7/2015 | Ryu | A61F 5/013 |
| | | | | 74/89.22 |
| 2015/0366277 | A1 | 12/2015 | Rabbeth, Jr. | |
| 2016/0287422 | A1 | 10/2016 | Kelly et al. | |
| 2016/0296345 | A1* | 10/2016 | Deshpande | A61F 2/586 |
| 2017/0042704 | A1* | 2/2017 | Ryu | A61H 1/0288 |

FOREIGN PATENT DOCUMENTS

| | | |
|---|---|---|
| JP | 3146959 U | 12/2008 |
| JP | 2009-112578 A | 5/2009 |
| JP | 2010-082342 A | 4/2010 |
| JP | 2014-001465 A | 1/2014 |
| JP | 2015-208511 A | 11/2015 |
| KR | 20-0328509 Y1 | 9/2003 |
| KR | 10-2011-0127252 A | 11/2011 |
| KR | 10-2012-0012675 A | 2/2012 |
| KR | 10-1541082 B1 | 8/2015 |
| KR | 10-2015-0121515 A | 10/2015 |
| KR | 10-2017-0056722 A | 5/2017 |
| KR | 10-2017-0081329 A | 7/2017 |
| WO | 91/11775 A1 | 8/1991 |
| WO | 2008/027002 A1 | 3/2008 |
| WO | 2012/018159 A1 | 2/2012 |
| WO | 2017/082635 A1 | 5/2017 |

OTHER PUBLICATIONS

An Office Action mailed by the Korean Intellectual Property Office dated Aug. 31, 2019, which corresponds to Korean Patent Application 10-2018-0113751 and is related to U.S. Appl. No. 16/189,715.
An Office Action mailed by the Korean Intellectual Property Office dated Jul. 31, 2020, which corresponds to Korean Patent Application 10-2019-0136684 and is related to U.S. Appl. No. 16/189,715.
An Office Action; "Notice of Reasons for Refusal", mailed by the Japanese Patent Office dated Jan. 19, 2021, which corresponds to Japanese Patent Application No. 2020-516848 and is related to U.S. Appl. No. 16/189,715.
The extended European search report issued by the European Patent Office dated Jul. 15, 2019, which corresponds to European Patent Application No. 18796567.8-1126 and is related to U.S. Appl. No. 16/189,715.
An Office Action mailed by China National Intellectual Property Administration dated Jul. 8, 2021, which corresponds to Chinese Patent Application No. 201880061977.0 and is related to U.S. Appl. No. 16/189,715.

* cited by examiner

APPARATUS FOR ASSISTING IN FINGER MOTION

CROSS-REFERENCE TO RELATED APPLICATIONS

The present application is a continuation of International Patent Application No. PCT/KR2018/011270, filed on Sep. 21, 2018, which is based upon and claims the benefit of priority to Korean Patent Application Nos. 10-2017-0123417, filed on Sep. 25, 2017 and 10-2018-0113751 filed on Sep. 21, 2018. The disclosures of the above-listed applications are hereby incorporated by reference herein in their entirety.

BACKGROUND

Embodiments of the inventive concept described herein relate to an apparatus for assisting in finger motion.

Spinal cord injury (SCI), stroke, Parkinson's disease, Lou Gehrig's disease, multiple sclerosis, cerebral palsy, and the like cause patients' hands to be paralyzed and constrain the patients from carrying out various actions required for everyday life, such as holding a cup with fingers and drinking water, tooth-brushing, turning a doorknob to open the door, and the like.

In particular, stroke or Parkinson's disease causes various physical changes depending on the condition and is accompanied by, for example, paralysis of hands and contracture of fingers. If the paralysis of the hands and the contracture of the fingers are just left continually, the muscles or joints become harder, and the patient may feel pain when moving and may have difficulty in normal activities even though the nerves are restored.

Furthermore, elderly people or rehabilitation patients with low muscular strength have difficulty in joint motion, compared to healthy people, and it is practically difficult to do exercise with general exercise equipment even though exercise is actually required.

To enable patients incapable of moving their fingers normally to perform finger motion like normal people, an apparatus for assisting the patients in moving their fingers is required.

SUMMARY

The inventive concept provides a finger motion assisting apparatus for providing an elastic force to straighten a finger and controlling finger motion according to a degree to which a wire is pulled, thereby enabling a patient having low muscular strength or incapable of freely moving fingers due to an abnormality in a nervous system to perform finger motion like a normal person.

The technical objects of the inventive concept are not limited to the above-mentioned ones, and the other unmentioned technical objects will become apparent to those skilled in the art from the following description.

In accordance with an aspect of the inventive concept, there is provided an apparatus for assisting in finger motion comprising: a wearing part; a first cover extending from the wearing part to one side; a first wire and a second wire configured to pull the first cover; a pulley around which the first wire and the second wire are wound; and a motor configured to rotate the pulley, wherein the first wire and the second wire are arranged from a first point of the first cover to a second point of the first cover along a direction in which the first cover extends and are arranged along at least part of a periphery of the first cover in opposite directions at the second point of the first cover.

In accordance with another aspect of the inventive concept, there is provided an apparatus for assisting in finger motion, the apparatus comprising: a wearing part; a first cover extending from the wearing part to one side; a first cover wire configured to pull the first cover; a pulley around which one end portion of the first cover wire is wound; and a motor configured to rotate the pulley, wherein the first cover wire is withdrawn from the pulley, extends along a direction in which the first cover extends, is wound along at least part of a periphery of the first cover, and extends along an opposite direction to the extension direction of the first cover, and an opposite end portion of the first cover wire is wound around the pulley.

The other detailed items of the inventive concept are described and illustrated in the specification and the drawings.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1A:
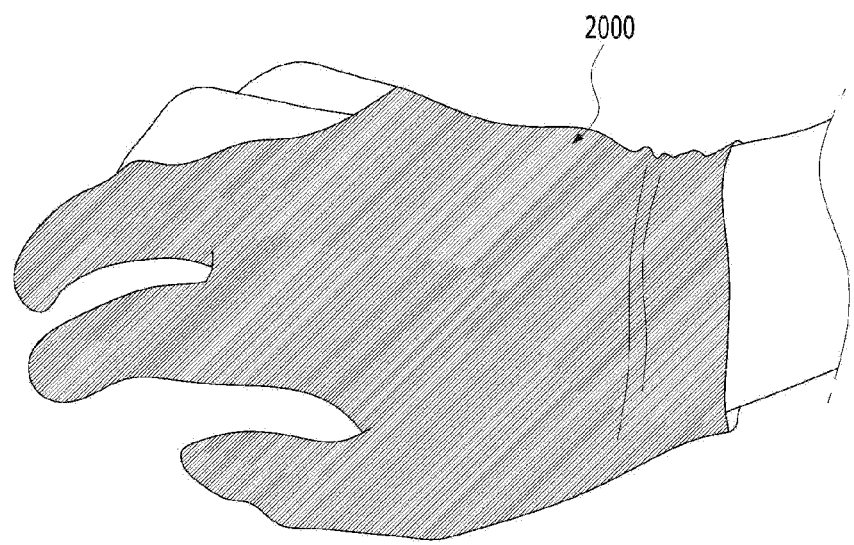
FIGS. 1A and 1B are views illustrating a state before a finger motion assisting apparatus of the inventive concept is worn.

The above and other aspects, features and advantages of the invention will become apparent from the following description of the following embodiments given in conjunction with the accompanying drawings. However, the inventive concept is not limited to the embodiments disclosed below, but may be implemented in various forms. The embodiments of the inventive concept are provided to make the disclosure of the inventive concept complete and fully inform those skilled in the art to which the inventive concept pertains of the scope of the inventive concept.

The terms used herein are provided to describe the embodiments but not to limit the inventive concept. In the specification, the singular forms include plural forms unless particularly mentioned. The terms "comprises" and/or "comprising" used herein does not exclude presence or addition of one or more other elements, in addition to the aforementioned elements. Throughout the specification, the same reference numerals dente the same elements, and "and/or" includes the respective elements and all combinations of the elements. Although "first", "second" and the like are used to describe various elements, the elements are not limited by the terms. The terms are used simply to distinguish one element from other elements. Accordingly, it is apparent that a first element mentioned in the following may be a second element without departing from the spirit of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

Hereinafter, exemplary embodiments of the inventive concept will be described in detail with reference to the accompanying drawings.

Figure 1B:
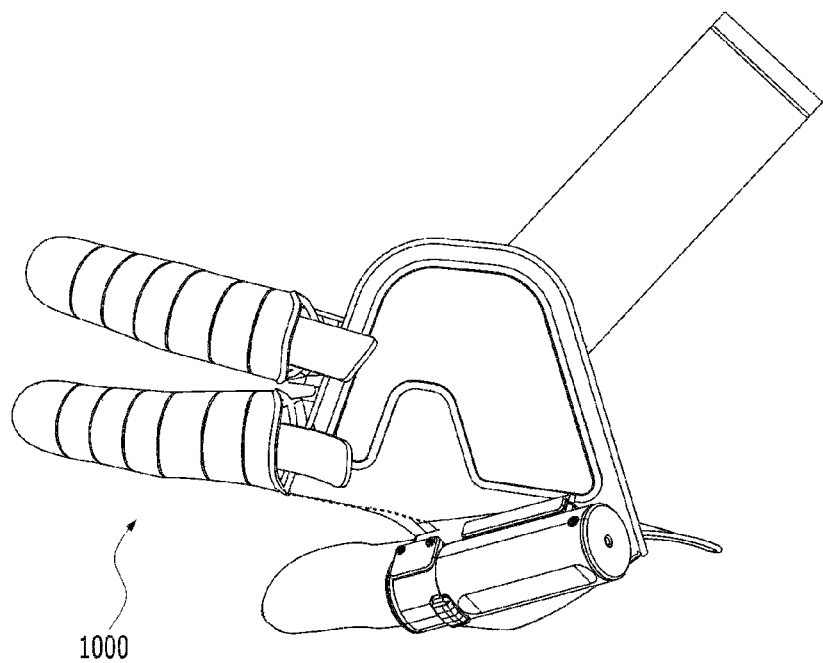
Figure 2:
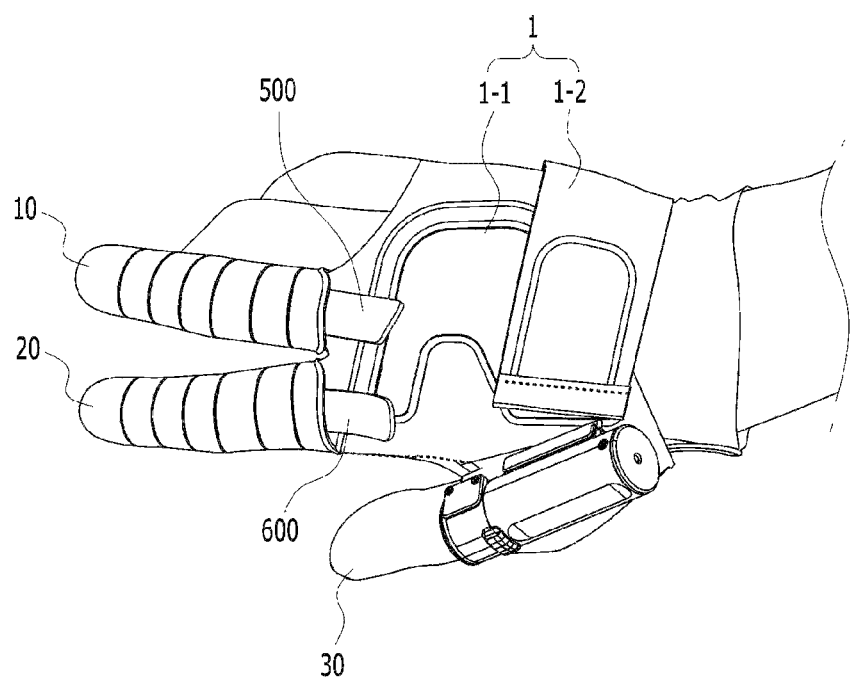
FIG. 2 is a view illustrating a state after the finger motion assisting apparatus of the inventive concept is worn.
Figure 3A:
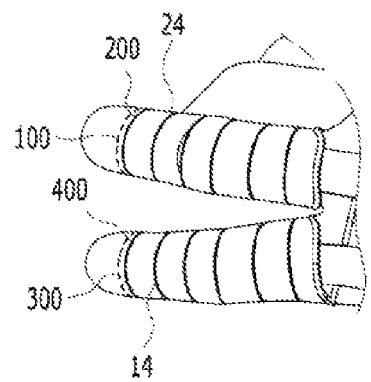
FIGS. 3A and 3B are views illustrating that a first wire and a second wire are disposed in the finger motion assisting apparatus of the inventive concept.
Figure 3B:
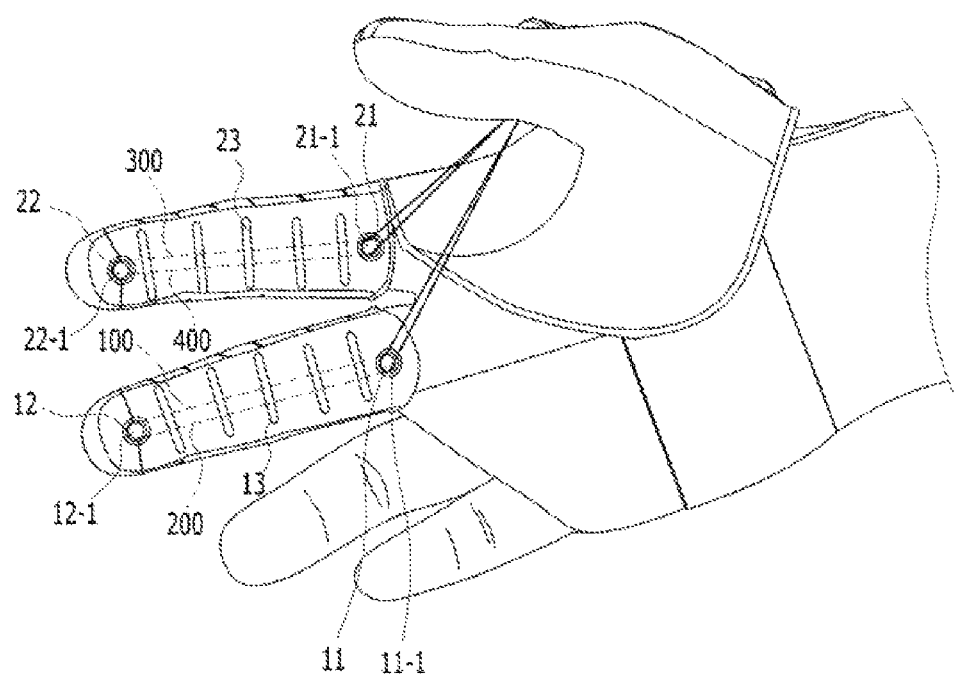
Figure 4:
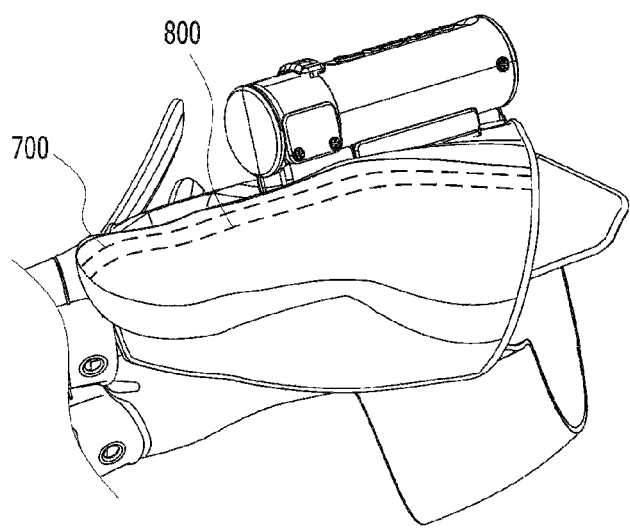
FIG. 4 is a view illustrating that a first auxiliary strap and a second auxiliary strap are disposed in the finger motion assisting apparatus of the inventive concept.
Figure 5A:
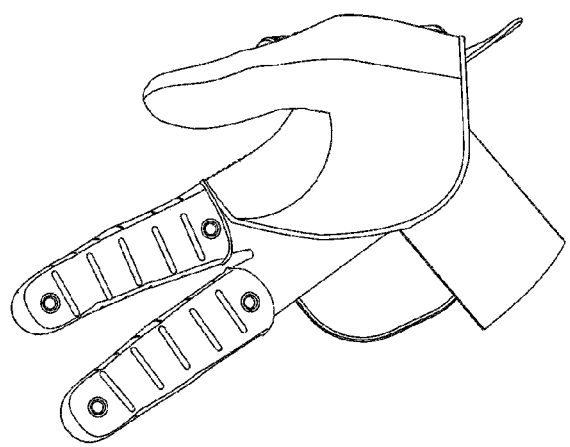
FIGS. 5A and 5B are views illustrating a C-grip and a pinch grip of the finger motion assisting apparatus of the inventive concept.
Figure 5B:
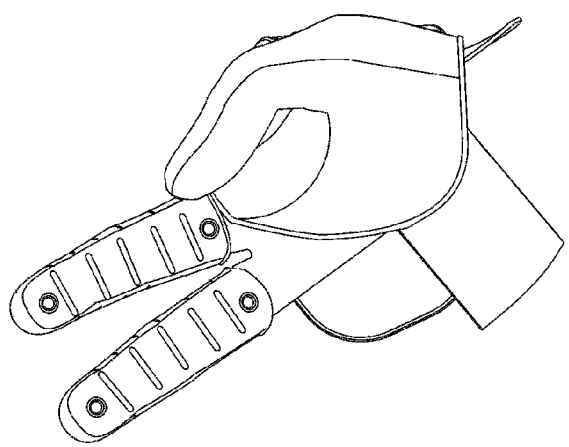
Figure 6A:
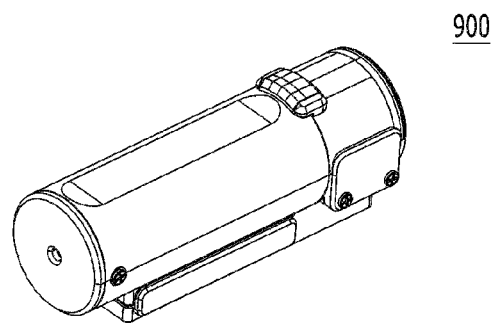
FIGS. 6A and 6B are views illustrating that a motor is mounted on the finger motion assisting apparatus of the inventive concept.
Figure 6B:
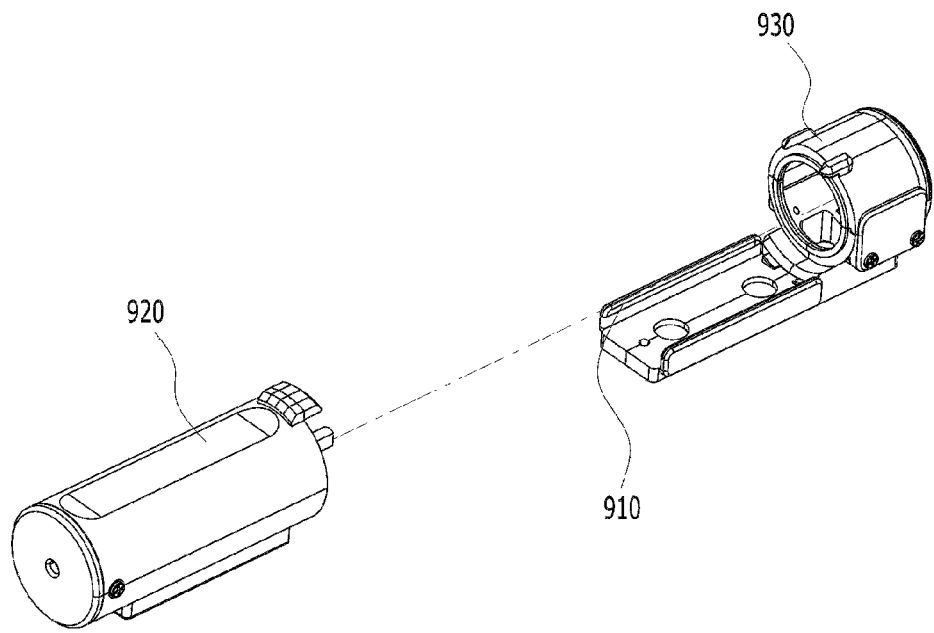
Figure 7:
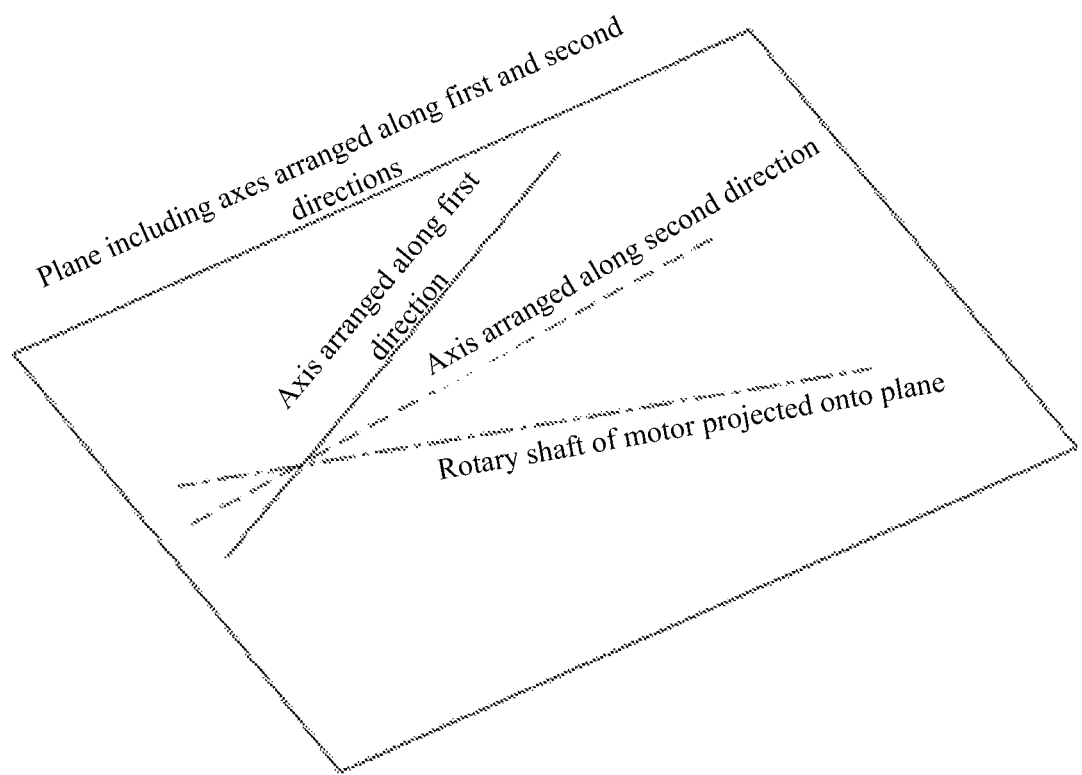
FIG. 7 is a schematic view illustrating that the rotary shaft of the motor of the inventive concept intersects an axis arranged along a first direction and an axis arranged along a second direction at one point.
Figure 8:
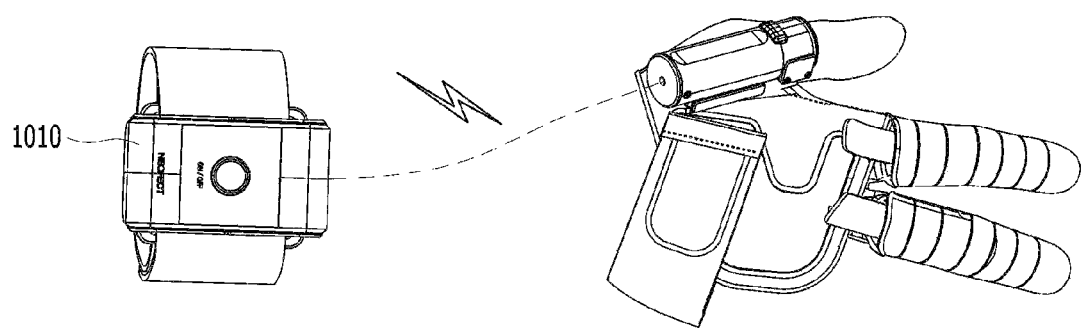
FIG. 8 is a view illustrating the finger motion assisting apparatus of the inventive concept and a remote controller.
Figure 9:
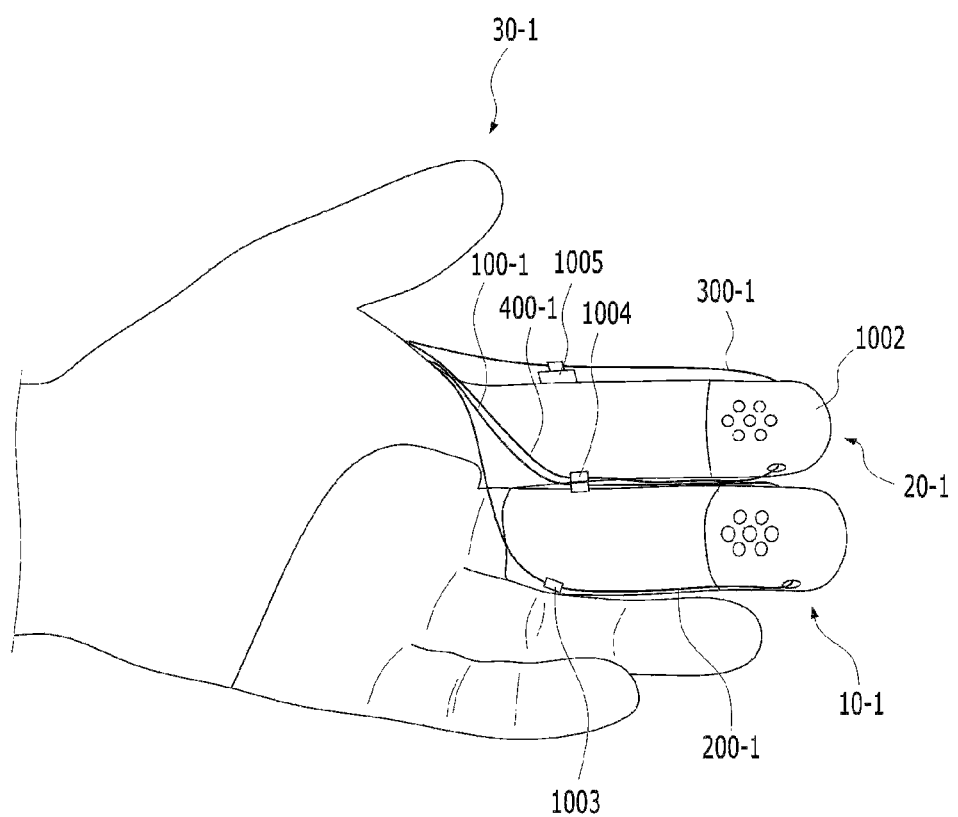
FIG. 9 is a view illustrating a finger motion assisting apparatus according to a first modified embodiment of the inventive concept.
Figure 10:
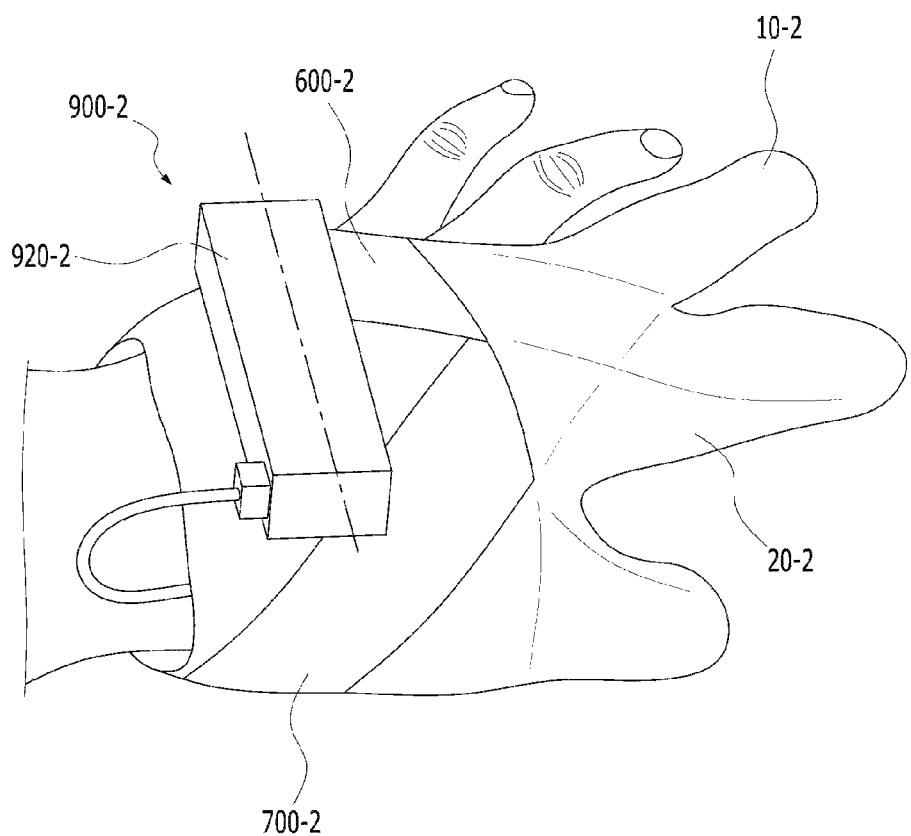
FIG. 10 is a view illustrating a finger motion assisting apparatus according to a second modified embodiment of the inventive concept.
Figure 11A:
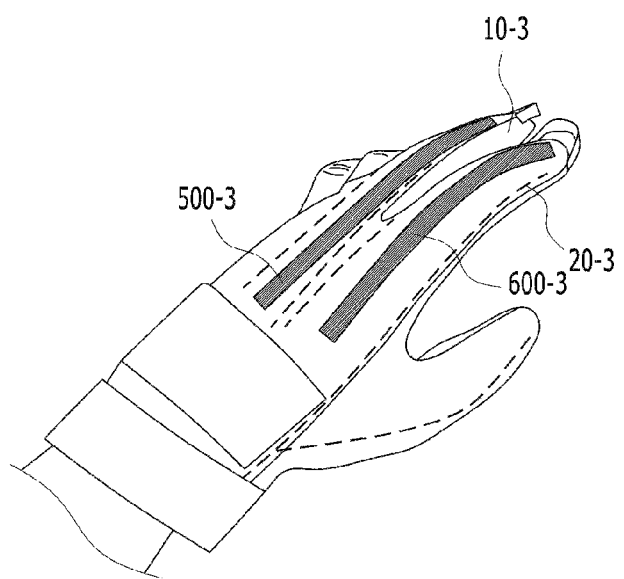
FIGS. 11A and 11B are views illustrating a finger motion assisting apparatus according to a third modified embodiment of the inventive concept.
Figure 11B:
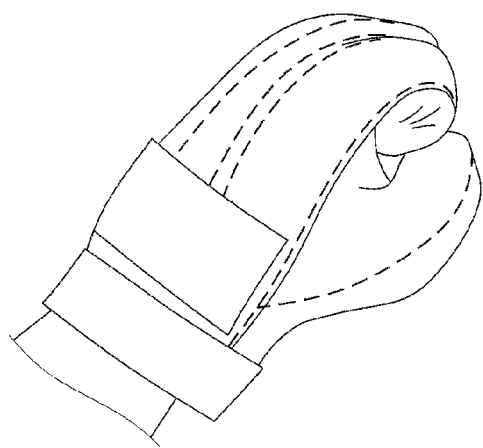
Figure 12A:
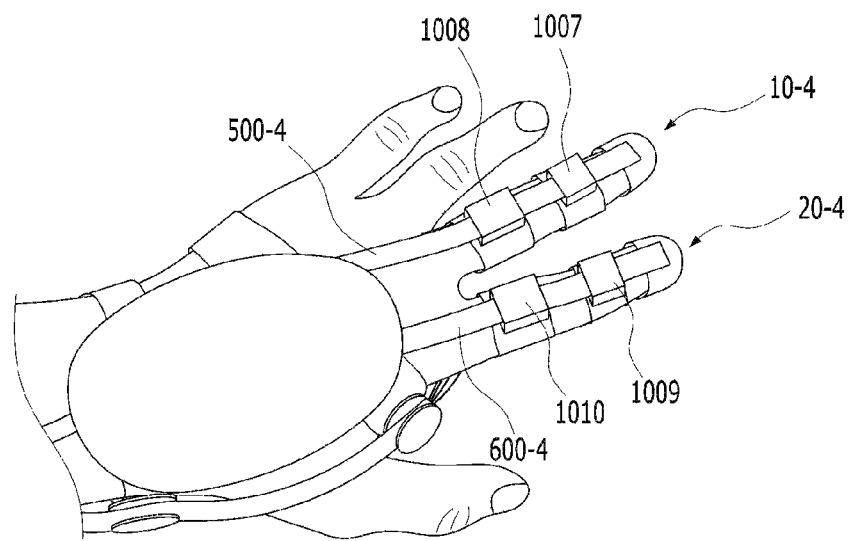
FIGS. 12A and 12B are views illustrating a finger motion assisting apparatus according to a fourth modified embodiment of the inventive concept.
Figure 12B:
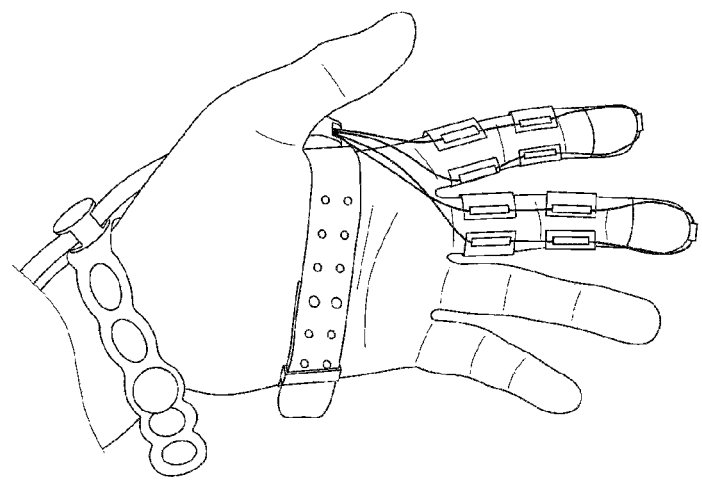

Hereinafter, a finger motion assisting apparatus 1000 of the inventive concept will be described with reference to the accompanying drawings. FIGS. 1A and 1B are views illustrating a state before the finger motion assisting apparatus of the inventive concept is worn. FIG. 2 is a view illustrating a state after the finger motion assisting apparatus of the inventive concept is worn. FIGS. 3A and 3B are views illustrating that a first wire and a second wire are disposed in the finger motion assisting apparatus of the inventive concept. FIG. 4 is a view illustrating that a first auxiliary strap and a second auxiliary strap are disposed in the finger motion assisting apparatus of the inventive concept. FIGS. 5A and 5B are views illustrating a C-grip and a pinch grip of the finger motion assisting apparatus of the inventive concept. FIGS. 6A and 6B are views illustrating that a motor is mounted on the finger motion assisting apparatus of the inventive concept. FIG. 7 is a schematic view illustrating that the rotary shaft of the motor of the inventive concept intersects an axis arranged along a first direction and an axis arranged along a second direction at one point. FIG. 8 is a view illustrating the finger motion assisting apparatus of the inventive concept and a remote controller. FIG. 9 is a view illustrating a finger motion assisting apparatus according to a first modified embodiment of the inventive concept. FIG. 10 is a view illustrating a finger motion assisting apparatus according to a second modified embodiment of the inventive concept. FIGS. 11A and 11B are views illustrating a finger motion assisting apparatus according to a third modified embodiment of the inventive concept. FIGS. 12A and 12B are views illustrating a finger motion assisting apparatus according to a fourth modified embodiment of the inventive concept.

Hereinafter, a side corresponding to the place where the palm of a wearer's hand is located may be defined as an "inside", and a side corresponding to the place where the back of the wearer's hand is located may be defined as an "outside".

The finger motion assisting apparatus 1000 of the inventive concept may be an auxiliary robot of a glove type that is worn by a patient or an elderly person having difficulty in gripping or holding an object due to a finger disorder or a weak finger force to provide an auxiliary force for finger motion.

The finger motion assisting apparatus 1000 of the inventive concept may assist in motions of the index and middle fingers of the wearer by traction of wires by a motor and may fix the wearer's thumb using the rigidities of a first support strap 500 and a second support strap 600. In this case, the shape in which the thumb is bent and the degree to which the thumb is bent may be modified by deforming the first support strap 500 and the second support strap 600.

The finger motion assisting apparatus 1000 of the inventive concept may be an open glove through which a portion of the wearer's hand is exposed. In addition, the wearer may put on an inner glove 2000 and may wear the finger motion assisting apparatus 1000 of the inventive concept over the inner glove 2000. This is intended to protect the wearer's hand and prevent slipping of the finger motion assisting apparatus 1000. In addition, at least a portion of a wearing part 1, a first cover 10, a second cover 20, or a third cover 30 may be formed of non-slip leather to more effectively prevent slipping of the finger motion assisting apparatus 1000 of the inventive concept.

The finger motion assisting apparatus 1000 of the inventive concept may include the wearing part 1, the first cover 10, the second cover 20, the third cover 30, a first wire 100, a second wire 200, a third wire 300, a fourth wire 400, the first auxiliary strap 500, the second auxiliary strap 600, a first support strap 700, a second support strap 800, and a driving module 900.

The wearing part 1 may surround at least part of the palm and back of the wearer's hand. The wearing part 1 may include a main body 1-1 having a Velcro formed or disposed on the outside thereof and a band 1-2 detachably coupled to the Velcro of the main body 1-1.

The first cover 10 may extend from the wearing part 1 in the first direction. The wearer's middle finger may be received in the first cover 10. The first cover 10 may be pulled and moved by the first wire 100 and the second wire 200. As a result, the first cover 10 may assist in motion of the middle finger of the wearer.

A first point 11 and a second point 12 sequentially spaced apart from each other in the extension direction of the first cover 10 may be located on an inner portion of the first cover 10. A hole 11-1 in which a rivet is disposed may be formed at the first point 11 of the first cover 10, and a hole 12-1 in which a rivet is disposed may be formed at the second point 12 of the first cover 10.

The first cover 10 may have a plurality of slits 13 formed in the inner portion thereof. The plurality of slits 13 may be spaced apart from each other along the extension direction of the first cover 10. Furthermore, the first cover 10 may have a plurality of slits 14 formed in an outer portion thereof. The plurality of slits 14 may be spaced apart from each other along the extension direction of the first cover 10. The plurality of slits 13 formed in the inner portion of the first cover 10 and the plurality of slits 14 formed in the outer portion of the first cover 10 may be formed in the direction of knuckles of the middle finger received in the first cover 10. Natural bending of the actual finger may be implemented by the plurality of slits 13 formed in the inner portion of the first cover 10 and the plurality of slits 14 formed in the outer portion of the first cover 10.

The second cover 20 may extend from the wearing part 1 in the second direction. The wearer's index finger may be received in the second cover 20. The second cover 20 may be pulled and moved by the third wire 300 and the fourth wire 400. As a result, the second cover 20 may assist in motion of the index finger of the wearer.

A first point 21 and a second point 22 sequentially spaced apart from each other in the extension direction of the second cover 20 may be located on an inner portion of the second cover 20. A hole 21-1 in which a rivet is disposed may be formed at the first point 21 of the second cover 20, and a hole 22-1 in which a rivet is disposed may be formed at the second point 22 of the second cover 20.

The second cover 20 may have a plurality of slits 23 formed in the inner portion thereof. The plurality of slits 23 may be spaced apart from each other along the extension direction of the second cover 20. Furthermore, the second cover 20 may have a plurality of slits 24 formed in an outer portion thereof. The plurality of slits 24 may be spaced apart from each other along the extension direction of the second cover 20. The plurality of slits 23 formed in the inner portion of the second cover 20 and the plurality of slits 24 formed in the outer portion of the second cover 20 may be formed in the direction of knuckles of the index finger received in the second cover 20. Natural bending of the actual finger may be implemented by the plurality of slits 23 formed in the inner portion of the second cover 20 and the plurality of slits 24 formed in the outer portion of the second cover 20.

The third cover 30 may extend from the wearing part 1 in a third direction. The wearer's thumb may be received in the third cover 30. The first support strap 700 and the second support strap 800 may be disposed inside the third cover 300. The third cover 30 may be fixed by the rigidities of the first support strap 700 and the second support strap 800. In addition, the shape of the third cover 30 may be modified depending on the shapes of the first support strap 700 and the second support strap 800. Accordingly, the materials of the first support strap 700 and the second support strap 800 may include a deformable rigid material. For example, the materials of the first support strap 700 and the second support strap 800 may include flexible metal such as aluminum. The shape in which the thumb is bent and the degree to which the thumb is bent may be diversely implemented by deforming the shape of the third cover 30.

The first wire 100 and the second wire 200 may pull the first cover 10. The first wire 100 and the second wire 200 may be wound around a pulley 930 of the driving module 900.

The first wire 100 and the second wire 200 may be arranged from the first point 11 of the first cover 10 to the second point 12 of the first cover 10 along the extension direction of the first cover 10. Furthermore, the first wire 100 and the second wire 200 may be arranged along at least part of the periphery of the first cover 10 in opposite directions at the second point 12 of the first cover 10.

The first wire 100 and the second wire 200 may be arranged on the inner portion of the first cover 10 along the extension direction of the first cover 10. In this case, the first wire 100 and the second wire 200 may sequentially pass through the hole 11-1 located at the first point 11 of the first cover 10 and the hole 12-1 located at the second point 12 of the first cover 10.

The first wire 100 and the second wire 200 may be arranged along at least part of the periphery of the first cover 10 and may be connected on the outer portion of the first cover 10. In this case, the first wire 100 and the second wire 200 may be connected together to form a single wire (may be integrally formed with each other). Furthermore, in this case, a receiving space for receiving the first wire 100 and the second wire 200 may be provided on the outer portion of the first cover 10.

As a result, when the first wire 100 and the second wire 200 are pulled, the first cover 10 may pull the middle finger to bend the middle finger. In this case, owing to the above-described arrangement of the first wire 100 and the second wire 200, the first cover 10 may be bent inward at the same time that the outer distal end of the first cover 10 is pulled, thereby naturally assisting in finger motion with high traction.

In the case where the first wire 100 and the second wire 200 are connected together to form a single wire, the first wire 100 and the second wire 200 may be referred to as the "first cover wire".

That is, one end portion of the first cover wire 100 and 200 may be wound around the pulley 930. The first cover wire 100 and 200 may be withdrawn from the pulley 930, may extend from the first point 11 of the first cover 10 along the extension direction of the first cover 10, may be wound along at least part of the periphery of the first cover 10 at the second point 12 of the first cover 10, may return to the second point 12 of the first cover 10, and may extend to the first point 11 of the first cover 10 in the opposite direction to the extension direction of the first cover 10, and an opposite end portion of the first cover wire 100 and 200 may be wound around the pulley 930.

In the case where the first cover wire 100 and 200 is wound along at least part of the periphery of the first cover 10, the first cover wire 100 and 200 may start from the inner portion of the first cover 10 and may return to the inner portion of the first cover 10 via the outer portion of the first cover 10.

The third wire 300 and the fourth wire 400 may pull the second cover 20. The third wire 300 and the fourth wire 400 may be wound around the pulley 930 of the driving module 900.

The third wire 300 and the fourth wire 400 may be arranged from the first point 21 of the second cover 20 to the second point 22 of the second cover 20 along the extension direction of the second cover 20. Furthermore, the third wire 300 and the fourth wire 400 may be arranged along at least part of the periphery of the second cover 20 in opposite directions at the second point 22 of the second cover 20.

The third wire 300 and the fourth wire 400 may be arranged on the inner portion of the second cover 20 along the extension direction of the second cover 20. In this case, the third wire 300 and the fourth wire 400 may sequentially pass through the hole 21-1 located at the first point 21 of the second cover 20 and the hole 22-1 located at the second point 22 of the second cover 20.

The third wire 300 and the fourth wire 400 may be arranged along at least part of the periphery of the first cover 20 and may be connected on the outer portion of the second cover 20. In this case, the third wire 300 and the fourth wire 400 may be connected together to form a single wire. Furthermore, in this case, a receiving space for receiving the third wire 300 and the fourth wire 400 may be provided on the outer portion of the second cover 20.

As a result, when the third wire 300 and the fourth wire 400 are pulled, the second cover 20 may pull the index finger to bend the index finger. In this case, owing to the above-described arrangement of the third wire 300 and the fourth wire 400, the second cover 20 may be bent inward at the same time that the outer distal end of the second cover 20 is pulled, thereby naturally assisting in finger motion with high traction.

In the case where the third wire 300 and the fourth wire 400 are connected together to form a single wire, the third wire 300 and the fourth wire 400 may be referred to as the "second cover wire".

That is, one end portion of the second cover wire 300 and 400 may be wound around the pulley 930. The second cover wire 300 and 400 may be withdrawn from the pulley 930, may extend from the first point 21 of the second cover 20 along the extension direction of the second cover 20, may be wound along at least part of the periphery of the second cover 20 at the second point 22 of the second cover 20, may return to the second point 22 of the second cover 20, and may extend to the first point 21 of the second cover 20 in the opposite direction to the extension direction of the second cover 20, and an opposite end portion of the second cover wire 300 and 400 may be wound around the pulley 930.

In the case where the second cover wire 300 and 400 is wound along at least part of the periphery of the second cover 20, the second cover wire 300 and 400 may start from the inner portion of the second cover 20 and may return to the inner portion of the second cover 20 via the outer portion of the second cover 20.

The first auxiliary strap 500 may extend from the wearing part 1 into the first cover 10. In this case, the first auxiliary strap 500 may be disposed inside the first cover 10. The first auxiliary strap 500 may be coupled to the outer portion of the first cover 10. Furthermore, a portion of the first auxiliary strap 500 exposed outside the first cover 10 may be detachably coupled to the Velcro of the main body 1-1 of the wearing part 1. The material of the first auxiliary strap 500 may include an elastic material with flexibility. For example, the material of the first auxiliary strap 500 may include Neopren.

The second auxiliary strap 600 may extend from the wearing part 1 into the second cover 20. In this case, the second auxiliary strap 600 may be disposed inside the second cover 20. The second auxiliary strap 600 may be coupled to the outer portion of the second cover 20. Furthermore, a portion of the second auxiliary strap 600 exposed outside the second cover 20 may be detachably coupled to the Velcro of the main body 1-1 of the wearing part 1. The material of the second auxiliary strap 600 may include an elastic material with flexibility. For example, the material of the second auxiliary strap 600 may include Neopren.

In summary, the first auxiliary strap 500 and the second auxiliary strap 600 may straighten the first cover 10 and the second cover 20 to implement stretch tension on the index and middle fingers of the wearer. In addition, the stretch tension on the wearer's index and middle fingers may be adjusted by changing the locations where the first auxiliary strap 500 and the second auxiliary strap 600 are attached to the Velcro of the main body 1-1 of the wearing part 1. As a result, the first auxiliary strap 500 and the second auxiliary strap 600 may adjust the stretch tension according to the degree of rigidity of the wearer's fingers to implement a neutral posture in design condition.

The first support strap 700 and the second support strap 800 may be disposed inside the third cover 300. The first support strap 700 and the second support strap 800 may be disposed adjacent to each other in the circumferential direction of the third cover 30. The first support strap 700 and the second support strap 800 may be arranged in the extension direction of the third cover 30.

The first support strap 700 and the second support strap 800 may have a flat plate shape. Furthermore, as described above, the materials of the first support strap 700 and the second support strap 800 may include metal. For example, the materials of the first support strap 700 and the second support strap 800 may include aluminum. As a result, the first support strap 700 and the second support strap 800 may ensure rigidity greater than or equal to a predetermined level to fix the thumb of the wearer, and when a force greater than or equal to a predetermined level is applied, the first support strap 700 and the second support strap 800 may be deformed to implement the shape in which the thumb of a normal person is bent and the degree to which the thumb is bent.

For example, as illustrated in FIG. 5A, the third cover 30 may be bent in a C-grip shape to implement a power grip, or as illustrated in FIG. 5B, the third cover 30 may be bent in a pinch grip shape to implement a shape advantageous for holding a small object.

The driving module 900 may provide a driving force to pull or release the first wire 100, the second wire 200, the third wire 300, and the fourth wire 400. The driving module 900 may include a bracket 910, a motor 920, and the pulley 930.

The bracket 910 may be disposed on the main body 1-1 of the wearing part 1. In this case, the bracket 910 may be disposed between the second cover 20 and the third cover 30.

The motor 920 and the pulley 930 may be mounted on the bracket 910. In this case, as illustrated in FIGS. 6A and 6B, the motor 920 may be removably mounted to the pulley 930 (FIG. 6A illustrates that the motor 920 is mounted to the pulley 930, and FIG. 6B illustrates that the motor 920 is separated from the pulley 930).

The pulley 930 may be rotated by the motor 920. The first wire 100, the second wire 200, the third wire 300, and the fourth wire 400 may be wound around the pulley 930. The first wire 100, the second wire 200, the third wire 300, and the fourth wire 400 may be wound around the pulley 930, or may be unwound from the pulley 930 and may be pulled or released, by the rotation of the pulley 930.

The rotary shaft of the motor 920 may form an acute angle with an axis arranged along the extension direction of the first cover 10 when projected onto a plane (e.g., a plane including the axis arranged in the extension direction of the first cover 10). In this case, the angle between the rotary shaft of the motor 920 and the axis arranged along the extension direction of the first cover 10 may range from 0 degrees to 80 degrees.

Likewise, the rotary shaft of the motor 920 may form an acute angle with an axis arranged along the extension direction of the second cover 20 when projected onto a plane (e.g., a plane including the axis arranged in the extension direction of the second cover 20). In this case, the angle between the rotary shaft of the motor 920 and the axis arranged along the extension direction of the second cover 20 may range from 0 degrees to 80 degrees.

Meanwhile, in the finger motion assisting apparatus 1000 of the inventive concept, the rotary shaft of the motor 920, when projected onto a plane including an axis arranged along the first direction (the extension direction of the first cover 10) and an axis arranged along the second direction (the extension direction of the second cover 20), may intersect the axis arranged along the first direction and the axis arranged along the second direction at approximately (substantially) one point.

That is, the rotary shaft of the motor 920 may intersect an extension line of the middle finger and an extension line of the index finger at the point where the extension line of the middle finger and the extension line of the index finger intersect each other. Accordingly, the first wire 100, the second wire 200, the third wire 300, and the fourth wire 400 may be prevented from being twisted. As a result, the first wire 100, the second wire 200, the third wire 300, and the fourth wire 400 may be continuously and stably pulled and released to implement accurate finger motion.

The finger motion assisting apparatus 1000 of the inventive concept may further include a remote controller 1010. The remote controller 1010 may include a power button, a grip button, and a release button. The wearer may press the power button to activate the remote controller 1010 and may press the grip button to perform a grip operation. In this case, the wires may be pulled by normal rotation of the motor 920. Furthermore, the wearer may press the release button to perform a release operation. In this case, the wires may be released by reverse rotation of the motor 920.

As illustrated in FIG. 8, the remote controller 1010 may be mounted in a wearable form on the wearer's arm by a band. In this case, the remote controller 1010 may be attached to or detached from the band by a magnetic force. Furthermore, the remote controller 1010 may be wirelessly or wiredly connected to the driving member 900. That is, signals of the remote controller 1010 may be transmitted to the driving module 900 through wireless communication or a conductive line.

A first modified embodiment of the inventive concept will hereinafter be described with reference to FIG. 9. The spirit of the above-described basic form of the inventive concept may be applied to the first modified embodiment of the inventive concept.

The first modified embodiment of the inventive concept differs from the basic form of the inventive concept in that the former includes a first cap 1001 and a second cap 1002 in a thimble form, and a first bracket 1003, a second bracket 1004, and a third bracket 1005 for supporting wires. Furthermore, the first modified embodiment of the inventive concept has a feature wherein a fifth wire (not illustrated) and a sixth wire (not illustrated) are separately disposed on a third cover 30-1 (a part for receiving at least part of a thumb).

The first cap 1001 may be disposed on an end portion of a first cover 10-1 (the end portion being oriented in the extension direction of the first cover 10-1), and the second cap 1002 may be disposed on an end portion of a second cover 20-1 (the end portion being oriented in the extension direction of the second cover 20-1). The first cap 1001 may cover at least part of the end portion of the first cover 10-1, and the second cap 1002 may cover at least part of the end portion of the second cover 20-1.

A first wire 100-1 and a second wire 200-1 may be arranged on the first cap 1001 along the extension direction of the first cover 10-1. In this case, the first wire 100-1 and the second wire 200-1 may be arranged on lateral portions of the first cover 10-1 (approximately, boundary portions between an outer portion and an inner portion of the first cover 10-1) along the extension direction of the first cover 10-1 so as to be spaced apart from each other.

To this end, a first bracket 1003 may be provided on a first lateral portion of the first cover 10-1 to support the first wire 100-1, and a second bracket 1004 may be provided on a second lateral portion of the first cover 10-1 to support the second wire 200-1.

The first wire 100-1 and the second wire 200-1 may be connected together in the first cap 1001. Furthermore, the first wire 100-1 and the second wire 200-1 may be wound around a driving member (not illustrated), as in the basic form of the inventive concept.

Likewise, a third wire 300-1 and a fourth wire 400-1 may be arranged on the second cap 1002 along the extension direction of the second cover 20-1. In this case, the third wire 300-1 and the fourth wire 400-1 may be arranged on lateral portions of the second cover 20-1 (approximately, boundary portions between an outer portion and an inner portion of the second cover 20-1) along the extension direction of the second cover 20-1 so as to be spaced apart from each other.

To this end, a third bracket 1005 may be provided on a first lateral portion of the second cover 20-1 to support the third wire 300-1, and the second bracket 1004 may be provided on a second lateral portion of the second cover 20-1 to support the fourth wire 400-1. That is, both the first wire 100-1 and the fourth wire 400-1 may be supported by the same second bracket 1004.

The third wire 300-1 and the fourth wire 400-1 may be connected together in the second cap 1002. Furthermore, the third wire 300-1 and the fourth wire 400-1 may be wound around the driving member (not illustrated), as in the basic form of the inventive concept.

In addition, in the first modified embodiment of the inventive concept, a fifth wire and a sixth wire may be provided on the third cover 30-1, and the third cover 30-1 may be moved by traction of the fifth and sixth wires by a motor. In this case, likewise to the first to fourth wires 100-1, 200-1, 300-1, and 400-1, the fifth and sixth wires may be wound around the driving member (not illustrated).

A second modified embodiment of the inventive concept will hereinafter be described with reference to FIG. 10. The spirit of the above-described basic form of the inventive concept may be applied to the second modified embodiment of the inventive concept.

The second modified embodiment of the inventive concept differs from the basic form of the inventive concept in terms of the form in which a first auxiliary strap 500-2 and a second auxiliary strap 600-2 are arranged and the form in which the rotary shaft of a motor 920-2 of a driving member 900-2 is arranged.

In this case, the first auxiliary strap 500-2 and the second auxiliary strap 600-2 may be arranged to cross each other. That is, the first auxiliary strap 500-2 and the second auxiliary strap 600-2 may extend to cross each other in first and second covers 10-2 and 20-2 and may be detachably coupled to the Velcro of the main body of 1-1 the wearing part 1. As a result, the wearer's index and middle fingers may be spaced apart from each other and supported by the first auxiliary strap 500-2 and the second auxiliary strap 600-2.

The rotary shaft of the motor 920-2 of the driving member 900-2, when projected onto a plane including an axis arranged along the first direction (the extension direction of the first cover 10-2) and an axis arranged along the second direction (the extension direction of the second cover 20-2), may intersect the axis arranged along the first direction and the axis arranged along the second direction at two points.

In this case, the rotary shaft of the motor 920-2 of the driving member 900-2 may be arranged such that the rotary shaft of the motor 920-2 of the driving member 900-2, the central axis of the first auxiliary strap 500-2 in the extension direction thereof, and the central axis of the second auxiliary strap 600-2 in the extension direction thereof approximately form an isosceles triangle on a plane.

A third modified embodiment of the inventive concept will hereinafter be described with reference to FIGS. 11A and 11B. The spirit of the above-described basic form of the inventive concept may be applied to the third modified embodiment of the inventive concept.

The third modified embodiment of the inventive concept differs from the basic form of the inventive concept in terms of the material and arrangement of a first auxiliary strap 500-3 and a second auxiliary strap 600-3.

The material of the first auxiliary strap 500-3 may include metal with high elasticity. Furthermore, the first auxiliary strap 500-3 may be disposed on the inside of an outer portion of a first cover 10-3. That is, the first cover 10-3 may have, on the outer portion thereof, a space for receiving the first auxiliary strap 500-3. To this end, the first cover 10-3 may have an auxiliary cover disposed thereon, and the space for receiving the first auxiliary strap 500-3 may be provided by sewing the auxiliary cover on the first cover 10-3.

The material of the second auxiliary strap 600-3 may include metal with high elasticity. Furthermore, the second auxiliary strap 600-3 may be disposed on the inside of an outer portion of a second cover 20-3. That is, the second cover 20-3 may have, on the outer portion thereof, a space for receiving the second auxiliary strap 600-3. To this end, the second cover 20-3 may have an auxiliary cover disposed thereon, and the space for receiving the second auxiliary strap 600-3 may be provided by sewing the auxiliary cover on the second cover 20-3.

According to the above description, in the third modified embodiment of the inventive concept, the first cover 10-3 and the second cover 20-3 may be straightened by the first auxiliary strap 500-3 and the second auxiliary strap 600-3 (the restoring forces of the auxiliary straps) to implement stretch tension on the wearer's index and middle fingers.

A fourth modified embodiment of the inventive concept will hereinafter be described with reference to FIGS. 12A and 12B. The spirit of the above-described basic form of the inventive concept may be applied to the fourth modified embodiment of the inventive concept.

The fourth modified embodiment of the inventive concept differs from the basic form of the inventive concept in that the former includes a strap driving member (not illustrated) for driving a first auxiliary strap 500-4 and a second auxiliary strap 600-4 and first to fourth guides 1007 to 1010 for guiding the first auxiliary strap 500-4 and the second auxiliary strap 600-4, and the first auxiliary strap 500-4 and the second auxiliary strap 600-4 are formed of a different material.

The first auxiliary strap 500-4 and the second auxiliary strap 600-4 may be formed of a flexible material. For example, the first auxiliary strap 500-4 and the second auxiliary strap 600-4 may be thin films made of a synthetic resin.

The first auxiliary strap 500-4 may be fixed to an end portion of a first cover 10-4 (the end portion being oriented in the extension direction of the first cover 10-4), and the second auxiliary strap 600-4 may be fixed to an end portion of a second cover 20-4 (the end portion being oriented in the extension direction of the second cover 20-4).

The first auxiliary strap 500-4 and the second auxiliary strap 600-4 may be pulled and moved by the separate strap driving member (not illustrated, a motor), and the first cover 10-4 and the second cover 20-4 may be straightened by this process. Accordingly, in the fourth modified embodiment of the inventive concept, stretch tension may be implemented on the wearer's index and middle fingers by the motor, and a neutral posture in design condition may be implemented by adjusting the stretch tension.

The first guide 1007 and the second guide 1008 may be disposed on the first cover 10-4 and may be spaced apart from each other along the extension direction of the first cover 10-4. The first auxiliary strap 500-4 may pass through the first guide 1007 and the second guide 1008 from the distal end of the first cover 10-4 and may be connected to the strap driving member. Accordingly, the first guide 1007 and the second guide 1008 may guide the moving direction of the first auxiliary strap 500-4, similarly to a rail.

Likewise, the third guide 1009 and the fourth guide 1010 may be disposed on the second cover 20-4 and may be spaced apart from each other along the extension direction of the second cover 20-4. The second auxiliary strap 600-4 may pass through the third guide 1009 and the fourth guide 1010 from the distal end of the second cover 20-4 and may be connected to the strap driving member. Accordingly, the third guide 1009 and the fourth guide 1010 may guide the moving direction of the second auxiliary strap 600-4, similarly to a rail.

According to the disclosed embodiment, the wires are withdrawn from the pulley, extend along the cover, surround the periphery of the cover near the distal end of the cover, extend along the cover again, and are wound around the pulley. That is, since two wires are disposed for each cover and the wires surround the periphery of the cover at the distal end of the cover, the cover is bent inward at the same time that the outer distal end of the cover is pulled by pulling the wires, thereby naturally assisting in finger motion with high traction.

Furthermore, since the rotary shaft of the motor intersects the axis arranged along the first direction and the axis arranged along the second direction at one point on a plane, twisting of the wires may be prevented. As a result, the wires may be continuously and stably pulled and released, thereby implementing accurate finger motion.

Moreover, since the first auxiliary strap and the second auxiliary strap are detachably coupled to the wearing part, it is possible to adjust stretch tension for straightening index and middle fingers, by adjusting the locations where the distal ends of the first and second auxiliary straps are attached to the wearing part. Accordingly, in the case where a wearer has ankylosis/contracture of a finger, stretch tension may be adjusted according to the degree of ankylosis/contracture, thereby implementing a neutral posture, with the finger sufficiently straightened.

In addition, since the first support strap and the second support strap are spaced apart from each other along the circumferential direction of the third cover (a thumb), bending of the thumb may be ergonomically accurately implemented.

Effects of the inventive concept are not limited to the aforementioned effects, and any other effects not mentioned herein will be clearly understood from the following description by those skilled in the art to which the inventive concept pertains.

Although the exemplary embodiments of the inventive concept have been described with reference to the accompanying drawings, it will be understood by those skilled in the art to which the inventive concept pertains that the inventive concept can be carried out in other detailed forms without changing the technical spirits and essential features thereof. Therefore, the above-described embodiments are exemplary in all aspects, and should be construed not to be restrictive.

What is claimed is:

1. An apparatus for assisting in finger motion, the apparatus comprising:
   a wearing part;
   a first cover extending from the wearing part to one side and being configured to substantially cover an entire finger of a user, the first cover having an interior surface facing a palm side surface of the user's finger and having an exterior surface opposite to the interior surface facing an external side of the first cover, wherein the first cover has a first opening and a second opening, the first opening corresponding to a proximal phalanx of the finger and the second opening positioned at a distal phalanx of the finger, the first opening and second opening being formed along the palm side surface of the finger, a first rivet disposed on the first opening, a circular face of the first rivet faces the palm side surface at the proximal phalanx of the finger and, a second rivet disposed on the second opening, a circular face of the second rivet faces the palm side surface at a distal phalanx of the finger;
   a first wire and a second wire configured to pull the first cover;
   a pulley around which the first wire and the second wire are wound; and
   a motor configured to rotate the pulley,
   wherein
   the first wire and the second wire are arranged from a first point, corresponding to the first opening, to a second point, corresponding to the second opening, along a first direction in which the first cover extends, the first wire and the second wire passing into the first opening at the first point, running along the interior surface of the first cover and exiting, via the second opening, to an exterior of the first cover,
   the first wire is, at the second point, after the first wire has exited the second opening is arranged to extend to a second direction along at least part of a circumference of the exterior surface of the first cover,
   the second wire is, at the second point, after the second wire has exited the second opening is arranged to extend to a third direction along at least another part of a circumference of the exterior surface of the first cover, and
   the second direction is an opposite direction to the third direction.

2. The apparatus of claim 1, wherein a receiving space for receiving the first wire and the second wire is provided on the exterior surface of the first cover, and at least part of the first wire and at least part of the second wire is not exposed to an outside through the exterior surface of the first cover.

3. The apparatus of claim 1, further comprising:
   a first auxiliary strap extending from the wearing part into the first cover,
   wherein the first auxiliary strap is configured to adjust a stretch tension of the first cover where the finger is being attached to.

4. The apparatus of claim 1, wherein a plurality of slits spaced apart from each other along the first direction are formed in an outer portion and an inner portion of the first cover, and
   wherein the plurality of slits of the first cover are formed in a direction of knuckles of the finger received in the first cover.

5. The apparatus of claim 1, further comprising:
   a second cover extending from the wearing part to a second side, disposed adjacent to the first cover, and comprising a second layer configured to substantially cover an entire second finger of the user, wherein the second cover has an opening disposed at one end of the second cover and configured to be positioned along a bottom of the second finger, and the second cover comprises a closed distal end disposed at the other end of the second cover and configured to be positioned at a tip of the second finger; and
   a third wire and a fourth wire configured to pull the second cover,
   wherein the third wire and the fourth wire are wound around the pulley, are arranged from a third point to a fourth point along a fourth direction in which the second cover extends,
   the fourth point is on the second cover and is configured to be positioned closer to a distal end of the second finger of the user than the third point that is on the second cover,
   the third wire is, at the fourth point, arranged to extend to a fifth direction along at least part of a circumference of the second cover,
   the fourth wire is, at the fourth point, arranged to extend to a sixth direction along at least another part of the circumference of the second cover, and
   the fifth direction is an opposite direction to the sixth direction.

6. The apparatus of claim 5, further comprising:
   a third cover extending from the wearing part to a third side, disposed adjacent to the second cover, and comprising a third layer configured to substantially cover an entire third finger of the user, wherein the third cover has an aopening disposed at one end of the third cover and configured to be positioned along a bottom of the third finger, and the third cover comprises a closed distal end disposed at the other end of the third cover and configured to be positioned at a tip of the third finger; and
   a first support strap and a second support strap disposed on the third cover,
   wherein the first support strap and the second support strap are disposed adjacent to each other in a circumferential direction of the third cover and are arranged along a seventh direction in which the third cover extends.

7. The apparatus of claim 1, wherein a rotary shaft of the motor forms an acute angle with an axis arranged along the first direction when projected onto a plane.

8. An apparatus for assisting in finger motion, the apparatus comprising:
   a wearing part;
   a first cover extending from the wearing part to one side and being configured to substantially cover an entire finger of a user, the first cover having an interior surface facing a palm side surface of the user's finger and having an exterior surface opposite to the interior surface facing an external side of the first cover, wherein the first cover has a first opening and a second opening, the first opening corresponding to a proximal phalanx of the finger and the second opening positioned at a distal phalanx of the finger, the first opening and second opening being formed along the palm side surface of the finger, a first rivet disposed on the first opening, a circular face of the first rivet faces the palm side surface at the proximal phalanx of the finger and, a second rivet disposed on the second opening, a circular face of the second rivet faces the palm side surface at a distal phalanx of the finger;
a first cover wire configured to pull the first cover;
a pulley; and
a motor configured to rotate the pulley,
wherein the first cover wire comprises:
  a first end portion that is wound around the pulley,
  a first portion that is directly connected with the first end portion and is withdrawn from the pulley;
  a second portion that is directly connected with the first portion and extends along a first direction in which the first cover extends; the second portion passing into the first opening, the second portion running along the interior surface of the first cover and exiting, via the second opening to an exterior of the first cover, a third portion that is directly connected with the second portion, the third portion being arranged on the exterior of the first cover after the second portion has exited the second opening, and is wound along at least part of a circumference of the exterior surface of the first cover;
  a fourth portion that is directly connected with the third portion, the fourth portion being arranged on the exterior of the first cover, and extends along an opposite direction to the first direction; and
  a second end portion that is directly connected with the fourth portion and is wound around the pulley.

9. An apparatus for assisting in finger motion, the apparatus comprising:
  a wearing part;
  a first cover extending from the wearing part to one side and being configured to substantially cover an entire finger of a user, the first cover having an interior surface facing a palm side surface of the user's finger and having an exterior surface opposite to the interior surface facing an external side of the first cover, wherein the first cover has a first opening and a second opening, the first opening corresponding to a proximal phalanx of the finger and the second opening positioned at a distal phalanx of the finger, the first opening and second opening being formed along the palm side surface of the finger, a first rivet disposed on the first opening, a circular face of the first rivet faces the palm side surface at the proximal phalanx of the finger and, a second rivet disposed on the second opening, a circular face of the second rivet faces the palm side surface at a distal phalanx of the finger;
  a first cover wire configured to pull the first cover;
  a second cover extending from the wearing part to another side and being configured to substantially cover an entire finger of a user, the second cover having an interior surface facing a palm side surface of the user's finger and having an exterior surface opposite to the interior surface facing an external side of the second cover, and the second cover being disposed adjacent to the first cover, wherein the second cover has a first opening and a second opening, the first opening corresponding to a proximal phalanx of the second finger and the second opening positioned at a distal phalanx of the second finger, the first opening and second opening being formed along the palm side surface of the second finger, a first rivet disposed on the first opening, a circular face of the first rivet faces the palm side surface at the proximal phalanx of the second finger and, a second rivet disposed on the second opening, a circular face of the second rivet faces the palm side surface at a distal phalanx of the second finger;
  a second cover wire configured to pull the second cover;
  a pulley around which the first cover wire and the second cover wire are wound;
  a motor configured to rotate the pulley, wherein the first cover wire is arranged from a first point of the first cover, corresponding to the first opening of the first cover, to a second point of the first cover, corresponding to the second opening of the first cover, along a first direction in which the first cover extends, the first cover wire passing into the first opening of the first cover at the first point of the first cover, running along the interior surface of the first cover and exit, via the second opening of the first cover, to an exterior of the first cover, the first cover wire is, at the second point of the first cover after the first cover wire has exited the second opening of the first cover, arranged along at least part of a circumference of the exterior surface of the first cover, wherein the second cover wire is arranged from a first point of the second cover, corresponding to the first opening of the second cover, to a second point of the second cover, corresponding to the second opening of the second cover, along a first direction in which the second cover extends, the second cover wire passing into the first opening of the second cover at the first point of the second cover, running along the interior surface of the second cover and exiting, via the second opening of the second cover, to an exterior of the second cover, the second cover wire is, at the second point of the second cover after the second cover wire has exited the second opening of the second cover, arranged along at least part of a circumference of the exterior surface of the second cover, wherein the motor
  and the pulley are configured to be positioned between a thumb and the second finger that is an index finger of the user.

10. The apparatus of claim 9, wherein the first cover wire comprises a first end portion that is arranged along at least part of the circumference of the first cover, and the first cover wire has a second end portion that is wound around the pulley, and
  wherein the second cover wire comprises a first end portion that is arranged along at least part of the circumference of the second cover, and the second cover wire has a second end portion that is wound around the pully.

* * * * *